United States Patent

Moreland

Patent Number: 5,413,598
Date of Patent: May 9, 1995

[54] VASCULAR GRAFT

[75] Inventor: Janet Moreland, Reading, Mass.

[73] Assignee: C. R. Bard, Inc., Murray Hill, N.J.

[21] Appl. No.: 275,815

[22] Filed: Jul. 15, 1994

Related U.S. Application Data

[63] Continuation of Ser. No. 37,028, Mar. 25, 1993, abandoned.

[51] Int. Cl.⁶ .......................... A61F 2/04; A61F 2/06
[52] U.S. Cl. .......................................... 623/1; 623/12; 600/36
[58] Field of Search .................... 623/1, 11, 12, 13; 600/36; 606/191, 192, 193, 194, 195, 152, 153, 154, 158

[56] References Cited

U.S. PATENT DOCUMENTS

| | | |
|---|---|---|
| 4,355,445 | 10/1982 | Matsumoto . |
| 4,632,842 | 12/1986 | Karwoski . |
| 4,652,263 | 3/1987 | Herweck . |
| 4,695,280 | 9/1987 | Watanabe et al. ................ 623/1 |
| 4,743,250 | 5/1988 | Kitigawa et al. ................ 623/1 |
| 4,990,158 | 2/1991 | Kaplan . |

FOREIGN PATENT DOCUMENTS

0501890A1  2/1992  European Pat. Off. .

OTHER PUBLICATIONS

Moore, Felix, "Air-Jet Texturing, Evolution of the Process", Nov. 27, 1990.

Steinmann, A. J., "Air-Jet Texturing and Interlacing, A Jet Technology and Market Development Update", Nov. 27, 1990.

Primary Examiner—David H. Willse
Assistant Examiner—Debra S. Brittingham
Attorney, Agent, or Firm—Wolf, Greenfield & Sacks

[57] ABSTRACT

A vascular graft fabric containing air jet textured yarns. The woven, knitted or braided fabric possesses a beneficial combination of strength, tissue infiltratability, handling and permeability.

7 Claims, 1 Drawing Sheet

VASCULAR GRAFT

This application is a continuation of application Ser. No. 08/037,028, filed Mar. 3, 1993, now abandoned.

FIELD OF INVENTION

The present invention relates to a vascular graft.

BACKGROUND OF THE INVENTION

Various synthetic vascular grafts have been proposed to replace, bypass or reinforce, diseased or damaged sections of a vein or artery. Commonly, tubular grafts have been formed from knitted or woven continuous filament polyester fiber (Dacron ®) and from expanded polytetrafluoroethylene (PTFE).

The performance of a vascular graft is influenced by certain characteristics such as strength, permeability, tissue ingrowth and ease of handling. A graft should be sufficiently strong to prevent the sidewalls from bursting when blood is flowing through the device even at high blood pressures. A graft also requires the strength necessary to maintain the patency of the vessel lumen.

A graft sidewall must be sufficiently impervious to blood to prevent hemorrhaging as blood flows through the graft. Expanded grafts are inherently leak resistant. Woven and knitted grafts, on the other hand, may require sealing of the openings between adjacent interlacings to prevent blood leakage. One procedure, pre-clotting, a woven or knitted graft is immersed in the patient's blood and then allowed to dry until the interstices in the vascular fabric become filled with the clotted blood. Another common technique is to coat the graft with an impervious material such as albumin, collagen or gelatin.

Tissue ingrowth through the interstices of the graft is believed to nourish and organize a thin neointima lining on the inner surface of a graft, preventing clotting of blood within the lumen of the graft which could occlude the graft. A velour surface may be provided on the outer surface of a woven or a knitted graft to encourage tissue infiltration. The pore size of a graft also influences tissue ingrowth. Although larger openings facilitate tissue penetration, pre-clotting or coating of the graft may be adversely affected as pore size increases.

Ease of handling is another important feature of a vascular graft. A flexible and conformable graft facilitates placement of the prosthesis by the surgeon. Increased elasticity, particularly of woven grafts has been achieved by crimping the graft. Crimping also improves resistance to kinking when the graft is bent or twisted.

Woven and knitted grafts generally have been formed from continuous filament polyester yarns which typically are textured prior to fabrication to impart bulk and stretch to the vascular graft fabric. A technique known as false twist texturing has been employed which involves the steps of twisting, heat setting and then untwisting the continuous multifilament yarns, providing substantially parallel, wavy filaments. A false twist textured yarn 1 is illustrated in FIG. 1. Staple fiber polyester yarns have not been used because of the concern that individual staple fibers may detach from the fabric and be carried away by the blood flow, forming an emboli.

Graft selection for a particular application has therefore involved trade-offs and compromises between one or more of the above properties. Expanded grafts provide strong structures which are non-porous and impervious to blood leakage. The absence of pores, however, precludes tissue ingrowth. Expanded PTFE grafts also may be stiff and nonconforming which detrimentally affects handleability. Knitted grafts have attractive tissue ingrowth and handleability features. The porous structure of knitted grafts, however, requires that the graft be pre-clotted or coated to prevent hemorrhaging. Woven grafts are less porous than knitted grafts and may not require pre-clotting or coating. The tightly compacted weave structure, however, may provide a stiff prosthetic which is not as conformable or as easily handled as is a knitted graft.

Attempts have been made to enhance the strength, permeability, tissue ingrowth and handling characteristics of synthetic vascular grafts by forming the prosthesis from very thin fibers having less than one denier per filament ("micro-denier"). Representative are U.S. Pat. Nos. 4,695,280 and 4,743,250 which disclose artificial vascular grafts which have been formed from a combination of micro-denier filament yarns and larger yarns.

SUMMARY OF THE INVENTION

The vascular graft fabric of the present invention displays a beneficial combination of strength, permeability, tissue infiltration and handleability. The fabric consists of interengaged air jet textured multifilament yarns which have been woven, knitted or braided into a seamless tubular configuration. Alternatively, a fabric sheet may be rolled into a cylinder and sewn along a seam to form a tubular product. Single and multiple lumen grafts (e.g., bifurcated, trifurcated, etc.) are contemplated.

In one embodiment of the invention, the vascular graft fabric consists of micro-denier filament yarns which have been air jet textured prior to their formation into a fabric structure. Larger yarns may be intertwined with the micro-denier filament yarns to strengthen the prosthesis.

It is among the general objects of the invention to provide a vascular graft fabric with an advantageous combination of strength, tissue ingrowth, resistance to blood leakage and handling characteristics.

Other objects and features of the present invention will become apparent from the following detailed description when taken in connection with the accompanying drawings which disclose multiple embodiments of the invention. It is to be understood that the drawings are intended for illustration only and not as a definition of the limits of the invention.

DESCRIPTION OF THE DRAWINGS

The foregoing and other objects and advantages of the invention will be appreciated more fully from the following drawings in which.

DESCRIPTION OF THE PREFERRED EMBODIMENTS

Figure 2:
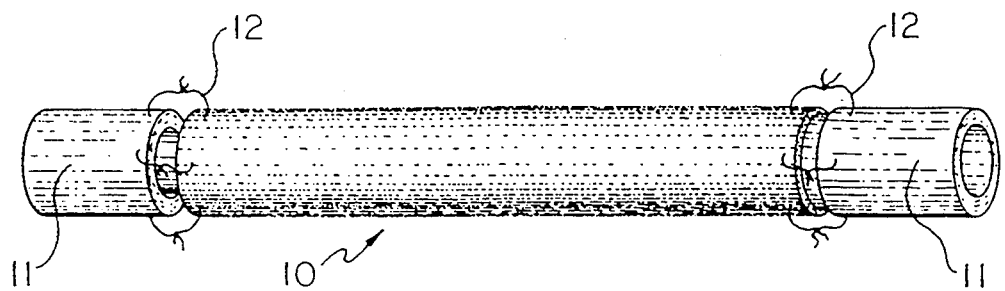
FIG. 2 is an illustration of a vascular graft according to the present invention.

The vascular graft 10 shown in FIG. 2 consists of interengaged air jet textured yarns which have been woven, knitted or braided into a tubular configuration.

After a diseased section of an artery or a vein has been removed, the vascular graft is joined to the exposed ends 11 of the healthy vessel. Although sutures 12 are illustrated, other arrangements for attaching the graft to a vein or artery, such as clamps, are contemplated. Prosthetic grafts including air jet textured yarns are expected to possess an advantageous combination of strength, permeability, tissue ingrowth and ease of handling.

Figure 3:
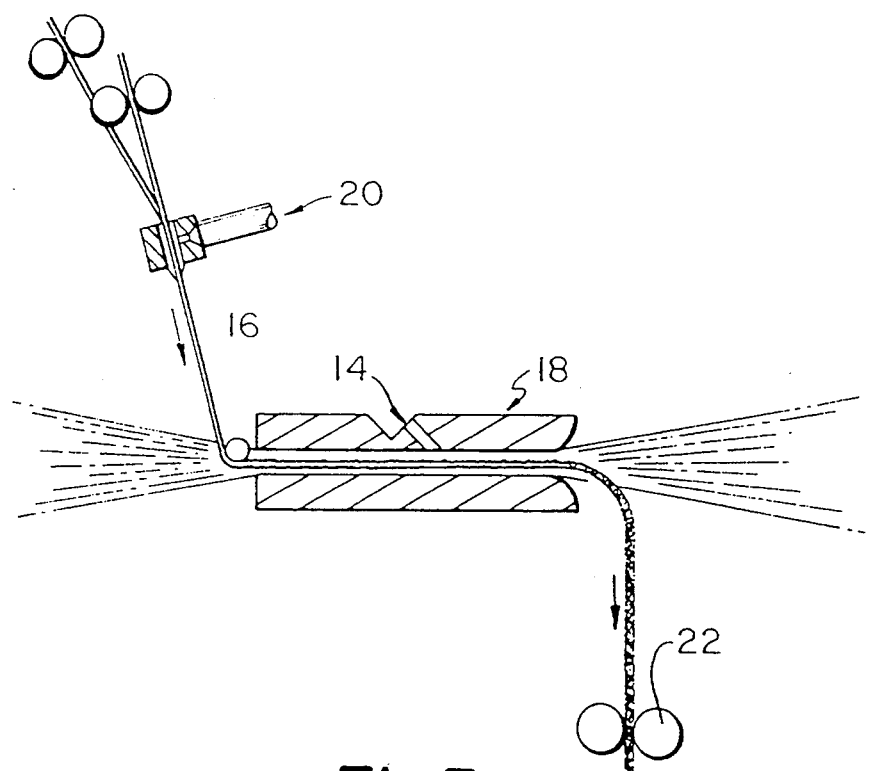
FIG. 3 is a schematic illustration of an air jet texturizing process for forming the yarns used in the present invention.
Figure 1:
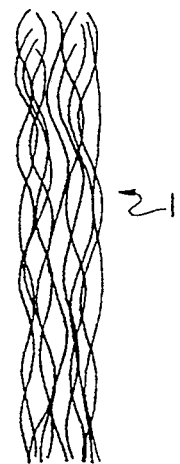
FIG. 1 is an illustration of a false twist textured yarn.

Air jet texturing is a technique, illustrated in FIG. 3, for imparting bulk to a yarn by jetting a high pressure stream of air 14 against a sheath yarn 16 which loops and tangles the sheath yarn about an underlying core yarn. The sheath and core yarns, each of which may include one or more yarns, are fed into a texturing chamber 18 at a faster speed than they are removed. The rate of overfeed, which may vary from 7 to 15 percent for the core yarn and from 10 to 30 percent for the sheath yarn, provides a filament slack or excess in the texturing chamber which becomes tangled by the turbulent air flow. Adjusting the overfeed differential and the level of air pressure in the texturing chamber may vary the number and size of the loops. The looping effect increases as the difference in the relative overfeed between the core and effect yarn increases. An increase in air pressure also encourages looping of the filaments, as well as compacting of the core yarn. Wetting the yarns in a water chamber 20 before entering the texturing chamber removes spinning finishes and reduces interfilament friction, encouraging filament entanglement. Downstream of the texturing chamber, the air jet textured yarn may be stabilized by passing the yarn against a heated pin or by collecting the yarn under tension in a pair of opposed rolls 22.

Figure 4:
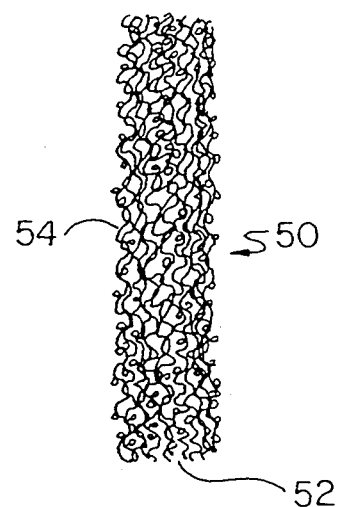
FIG. 4 is an illustration of an air jet textured yarn.

The resulting air jet textured yarn 50, illustrated in FIG. 4, includes a core 52 of essentially straight filaments and an outer layer 54 of small, compact loops which are firmly entangled with the core filaments.

A synthetic polyester fiber (such as Dacron®) is a preferred material for forming the air jet textured graft fabric. Other contemplated yarn materials are nylon and polypropylene. Air jet textured yarns formed of micro-denier filaments (e.g., having less than or equal to one denier per filament) appear to be advantageous, providing numerous small, entangled loops which are quickly stabilized by hot pin rolling. Vascular grafts formed from such fine yarns are expected to be more easily handled and sutured while providing increased strength, decreased fraying, resistance to suture pullout and blood leakage. Larger yarns, having a denier to filament ratio greater than one, and which have not been air jet textured, may be incorporated into the vascular fabric to reinforce and further strengthen the graft.

Before implantation, the vascular graft may be cleaned to remove oils or other impurities remaining from manufacturing. Chemical or thermal compacting may also be employed to reduce the fabric porosity, increasing the resistance to hemorrhaging. The tubular graft may be crimped to improve flexibility, preventing kinking or occlusion of the graft lumen when the prosthesis is manipulated to conform to the anatomical site. Rapid tissue ingrowth which leads to the formation of a neointima lining along the graft lumen may be encouraged by providing a velour structure on the surface of the graft.

In order to further illustrate the invention, the following examples are provided. It is to be understood, however, that the examples are included for illustrative purposes only and are not intended to limit the scope of the invention as set forth in the accompanying claims.

EXAMPLES

Normalized radial tensile analysis (strength) was conducted on an Instron 4202 arranged with radial tensile jaws and a 200 lb load cell. Crosshead speed was ten inches per minute with proportions of 1:1. Half inch long greige samples were mounted in the jaws of the Instron and were pulled until failure. Several samples were tested providing an average tensile strength.

Pore size was determined in a Coulter® Porometer II which calculates the pore size of a fabric based on the amount of fluid that flows through the fabric at incremental pressures. Samples were soaked in Porofil, a wetting agent, to wet the pores. Breathing quality compressed air was then forced through the samples at incremental pressures. Theoretically, a greater force is required to displace a fluid through a smaller pore.

Handling characteristics were tested subjectively and by a Kawabata surface roughness test which involves tensioning fabric samples at 400 and 1000 gram force values. Friction and roughness probes with 10 gram force were conducted in both the forward and backward directions.

Permeability represents the amount of water that flows through a square centimeter of fabric in one minute at a pressure of 120 mm Hg. Flat fabric samples were mounted about a testing orifice and then were prewetted to minimize the effect of entrapped air or microbubbles attached to the material surface. The test was conducted pursuant to the American National Standard for Vascular Graft Prostheses 4.3.1.2(1)(b).

EXAMPLE 1

A tubular fabric was woven in a 2×1 basic twill pattern. The fabric included 160 ends per inch and 360 picks per inch. The fill yarns were air jet texturized 170 denier 258 filament Dacron® polyester. The warp yarns were 2 ply 50 denier/47 filament polyester yarns which were false twist texturized. Alternate filling yarns floated over five warp ends, created a velour affect for encouraging tissue infiltration.

The air jet texturized yarns were made by drawing two 110 denier/129 filament yarns down to 70 denier prior to entering the texturing chamber. The core yarn was run at a 10 percent overfeed and the effect yarn was run with 30 percent overfeed. The air pressure in the texturing chamber was 135 psi. The yarn loops were stabilized by passing the yarns over a heater pin having a temperature of approximately 200° C.

Av. Tensile Str.: 125.0 lb/inch
Permeability: 513.3 cc/cm$^2$/min.
Pore Size: 12.5 microns (mean flow pore size)
Surface Roughness Index (400 g):
  Outside: 4.88 (greige) 22.89 (crimped)
  Inside: 2.98 (greige) 13.19 (crimped)

EXAMPLE 2

A tubular vascular graft was woven in a plain weave pattern with approximately 80 ends per inch and 150 picks per inch. The filling yarn was an air jet texturized, micro-denier filament yarn (170 denier/258 filament Dacron®). The core yarn was run with a 10 percent overfeed and the sheath yarn was textured with a 30 percent overfeed. The air pressure and stabilizing temperature were comparable to the levels recited in Example 1.

Av. Tensile Str.: 104.0 lb/inch
Permeability: 645.0 cc/cm²/min.
Pore Size: 12.04 microns (mean flow pore size)
Surface Roughness Index (400 g):
    Outside: 6.99 (greige) 21.50 (crimped)
    Inside: 4.26 (greige) 12.84 (crimped)

EXAMPLE 3

A tubular fabric having 52 courses per inch was warp knitted in a reverse locknit pattern on a 64 gauge Raschel machine. The front bar and back bar yarns were 150 denier/200 filament air jet textured polyester which had been drawn from two 100 denier/100 filament yarns prior to texturing. The overfeed rate of the core yarn was 10 percent and of the sheath yarn was 30 percent. A velour effect was created using a runner length on the front bar set at 28 inches.

Although quantitative tests were not conducted on the knitted prosthesis, subjective analysis indicates that the knitted graft fabric has excellent handling characteristics.

With respect to Examples 1 and 2, the Kawabata surface roughness test did not differentiate the air jet textured yarn fabrics from graft structures formed from conventional yarns. Subjective analysis, however, indicated that the air jet textured materials provide a dramatic improvement in handleability. The use of the Kawabata system to quantify handling of vascular grafts therefore requires further investigation.

It should be understood that the foregoing description of the invention is intended merely to be illustrative thereof and that other equivalents, embodiments and modifications of the invention may be apparent to those skilled in the art.

We claim:

1. A vascular graft comprising individual air jet textured yarns each of which includes a core of at least one essentially straight filament and an outer layer of small, compact loops which are firmly entangled with said at least one core filament, said individual air jet textured yarns being interengaged into a fabric structure which is constructed and arranged in a tubular configuration and has a lumen for conveying blood therethrough.

2. The vascular graft recited in claim 1 wherein at least a portion of said air jet textured yarns include micro-denier filament yarns.

3. The vascular graft recited in claim 1 further including yarns which have not been air jet textured which are interengaged with said air jet textured yarns.

4. The vascular graft recited in claim 3 wherein said air jet textured yarns include micro-denier filament yarns and said yarns which have not been air jet textured have a denier to filament ratio greater than one.

5. A woven vascular graft comprising warp yarns, and individual filling yarns which have been air jet textured, each of said filling yarns including a core of at least one essentially straight filament and an outer layer of small, compact loops which are firmly entangled with said least one core filament, said warp and air jet textured filling yarns being woven together into a fabric structure which is constructed and arranged in a tubular configuration and has a lumen for conveying blood therethrough.

6. The woven vascular graft recited in claim 5 wherein said air jet textured yarns include micro-denier filament yarns.

7. A vascular graft containing individual air jet textured micro-denier filament yarns each of which includes a core of at least one essentially straight filament and an outer layer of small, compact loops which are firmly entangled with said at least one core filament, said micro-denier filament yarns being interengaged into a seamless tubular fabric structure.

* * * * *